(12) United States Patent
Forsberg et al.

(10) Patent No.: US 10,967,107 B2
(45) Date of Patent: Apr. 6, 2021

(54) SUCTION AND IRRIGATION DEVICE

(71) Applicant: ENTELLUS MEDICAL, INC., Maple Grove, MN (US)

(72) Inventors: Andrew T. Forsberg, Plymouth, MN (US); John R. Drontle, Buffalo, MN (US); Anthony J. Hanson, Chaska, MN (US)

(73) Assignee: Entellus Medical, Inc., Maple Grove, MN (US)

( * ) Notice: Subject to any disclaimer, the term of this patent is extended or adjusted under 35 U.S.C. 154(b) by 145 days.

(21) Appl. No.: 16/075,081

(22) PCT Filed: Apr. 28, 2016

(86) PCT No.: PCT/US2016/029639
§ 371 (c)(1),
(2) Date: Aug. 2, 2018

(87) PCT Pub. No.: WO2017/135980
PCT Pub. Date: Aug. 10, 2017

(65) Prior Publication Data
US 2019/0038817 A1 Feb. 7, 2019

Related U.S. Application Data

(60) Provisional application No. 62/290,882, filed on Feb. 3, 2016.

(51) Int. Cl.
*A61M 1/00* (2006.01)
*A61M 3/02* (2006.01)
(Continued)

(52) U.S. Cl.
CPC ........ *A61M 1/0064* (2013.01); *A61M 1/0084* (2013.01); *A61M 3/0283* (2013.01);
(Continued)

(58) Field of Classification Search
CPC .. A61M 1/0064; A61M 3/0283; A61M 25/02; A61M 1/0084; A61M 2210/0681;
(Continued)

(56) References Cited

U.S. PATENT DOCUMENTS 3,109,426 A 11/1963 Noonan et al.
4,031,896 A 6/1977 Ronnmark
(Continued)

FOREIGN PATENT DOCUMENTS

JP H06-327774 A 11/1994
JP 2000-237201 A 9/2000
(Continued)

OTHER PUBLICATIONS

PCT International Search Report for PCT/US2016/029639, Applicant: Entellus Medical, Inc., Form PCT/ISA/210 and 220, dated Jul. 29, 2016 (3pages).
(Continued)

*Primary Examiner* — Lauren P Farrar
(74) *Attorney, Agent, or Firm* — McDonnell Boehnen Hulbert & Berghoff LLP

(57) ABSTRACT

Described herein are devices and methods for irrigating and suctioning fluids from the lumens or cavities of a mammalian body. The devices include a malleable irrigation tube and a suction tube that is slidably mounted upon the irrigation tube.

25 Claims, 10 Drawing Sheets

(51) Int. Cl.
*A61M 25/02* (2006.01)
*A61B 1/015* (2006.01)
*A61B 17/24* (2006.01)

(52) U.S. Cl.
CPC ............. *A61M 25/02* (2013.01); *A61B 1/015* (2013.01); *A61B 17/24* (2013.01); *A61M 2205/582* (2013.01); *A61M 2210/0618* (2013.01); *A61M 2210/0681* (2013.01)

(58) Field of Classification Search
CPC .... A61M 2210/0618; A61M 2205/582; A61B 17/24; A61B 1/015
See application file for complete search history.

(56) References Cited

U.S. PATENT DOCUMENTS

| | | | |
|---|---|---|---|
| 4,102,342 A | | 7/1978 | Akiyama et al. |
| 4,400,168 A | | 8/1983 | Buechel et al. |
| 5,024,658 A | | 6/1991 | Kozlov et al. |
| 5,562,640 A | | 10/1996 | McCabe et al. |
| 6,033,404 A | * | 3/2000 | Melzer ............... A61B 18/1482 606/41 |
| 6,471,667 B1 | * | 10/2002 | Epstein ............ A61B 17/00491 137/625.4 |
| 6,679,834 B2 | | 1/2004 | Stahl et al. |
| 6,986,757 B1 | | 1/2006 | Kumasaki et al. |
| 7,520,876 B2 | | 4/2009 | Ressemann et al. |
| 7,678,099 B2 | | 3/2010 | Ressemann et al. |
| 7,842,062 B2 | | 11/2010 | Keith et al. |
| 7,879,061 B2 | | 2/2011 | Keith et al. |
| 7,918,871 B2 | | 4/2011 | Truitt et al. |
| 8,241,266 B2 | | 8/2012 | Keith et al. |
| 8,277,478 B2 | | 10/2012 | Drontle et al. |
| 8,282,667 B2 | | 10/2012 | Drontle et al. |
| 8,348,969 B2 | | 1/2013 | Keith et al. |
| 8,568,439 B2 | | 10/2013 | Keith et al. |
| 8,585,728 B2 | | 11/2013 | Keith et al. |
| 8,585,729 B2 | | 11/2013 | Keith et al. |
| 8,623,043 B1 | | 1/2014 | Keith et al. |
| 8,657,846 B2 | | 2/2014 | Keith et al. |
| 8,801,670 B2 | | 8/2014 | Drontle et al. |
| 8,834,513 B2 | | 9/2014 | Hanson et al. |
| 8,882,795 B2 | | 11/2014 | Drontle et al. |
| 8,888,686 B2 | | 11/2014 | Drontle et al. |
| 8,915,938 B2 | | 12/2014 | Keith et al. |
| 9,005,284 B2 | | 4/2015 | Ressemann |
| 9,101,739 B2 | | 8/2015 | Lesch, Jr. et al. |
| 9,192,748 B2 | | 11/2015 | Ressemann et al. |
| 9,278,199 B2 | | 3/2016 | Keith et al. |
| 9,282,986 B2 | | 3/2016 | Hanson et al. |
| 9,283,360 B2 | | 3/2016 | Lesch et al. |
| 9,320,876 B2 | | 4/2016 | Ressemann et al. |
| 9,333,327 B2 | | 5/2016 | Setliff, III et al. |
| 9,339,637 B2 | | 5/2016 | Drontle et al. |
| 9,370,650 B2 | | 6/2016 | Hanson et al. |
| 9,433,343 B2 | | 9/2016 | Drontle et al. |
| 9,440,049 B2 | | 9/2016 | Drontle et al. |
| 9,486,614 B2 | | 11/2016 | Drontle et al. |
| 9,550,049 B2 | | 1/2017 | Hanson et al. |
| 9,694,167 B2 | | 7/2017 | Keith et al. |
| 9,700,705 B2 | | 7/2017 | Lesch, Jr. et al. |
| 9,775,975 B2 | | 10/2017 | Ressemann et al. |
| 10,022,525 B2 | | 7/2018 | Hanson et al. |
| 10,029,069 B2 | | 7/2018 | Keith et al. |
| 10,086,181 B2 | | 10/2018 | Lesch |
| 2004/0243157 A1 | | 12/2004 | Connor et al. |
| 2005/0273063 A1 | | 12/2005 | Hoell et al. |
| 2008/0172033 A1 | | 7/2008 | Keith et al. |
| 2010/0312101 A1 | * | 12/2010 | Drontle ............... A61B 17/24 600/424 |
| 2011/0282195 A1 | | 11/2011 | Solar et al. |
| 2013/0030458 A1 | | 1/2013 | Drontle et al. |
| 2013/0072958 A1 | * | 3/2013 | Ressemann ........... A61B 17/24 606/199 |
| 2016/0151614 A1 | | 6/2016 | Ressemann et al. |
| 2016/0166814 A1 | | 6/2016 | Lesch et al. |
| 2016/0367286 A1 | | 12/2016 | Drontle et al. |
| 2017/0007282 A1 | | 1/2017 | Drontle et al. |
| 2017/0028112 A1 | | 2/2017 | Drontle et al. |
| 2017/0050001 A1 | | 2/2017 | Drontle et al. |
| 2017/0113027 A1 | | 4/2017 | Drontle et al. |
| 2017/0368319 A1 | | 12/2017 | Lesch, Jr. et al. |
| 2018/0008806 A1 | | 1/2018 | Ressemann et al. |
| 2018/0304051 A1 | | 10/2018 | Keith et al. |
| 2018/0304058 A1 | | 10/2018 | Hanson et al. |

FOREIGN PATENT DOCUMENTS

| | | |
|---|---|---|
| JP | 2012-258702 A | 11/2012 |
| WO | 01/30416 A1 | 5/2001 |
| WO | 2010/141894 A1 | 12/2010 |

OTHER PUBLICATIONS

PCT Written Opinion of the International Search Authority for PCT/US2016/029639, Applicant: Entellus Medical, Inc., Form PCT/ISA/237, dated Jul. 29, 2016 (6pages).
Response to Written Opinion of the International Search Authority dated Aug. 31, 2016 in International Application No. PCT/US2016/029639, dated Aug. 31, 2016 (4pages).
PCT International Preliminary Report on Patentability (Chapter II of the Patent Cooperation Treaty) for PCT/US2016/029639, Applicant: Entellus Medical, Inc., dated Nov. 9, 2017 (18pages).
English Translation of Abstract of Japanese Patent Application No. H06327774 dated Mar. 10, 2020.
English Translation of Abstract of Japanese Patent Application No. 2000-237201 dated Mar. 10, 2020.

* cited by examiner

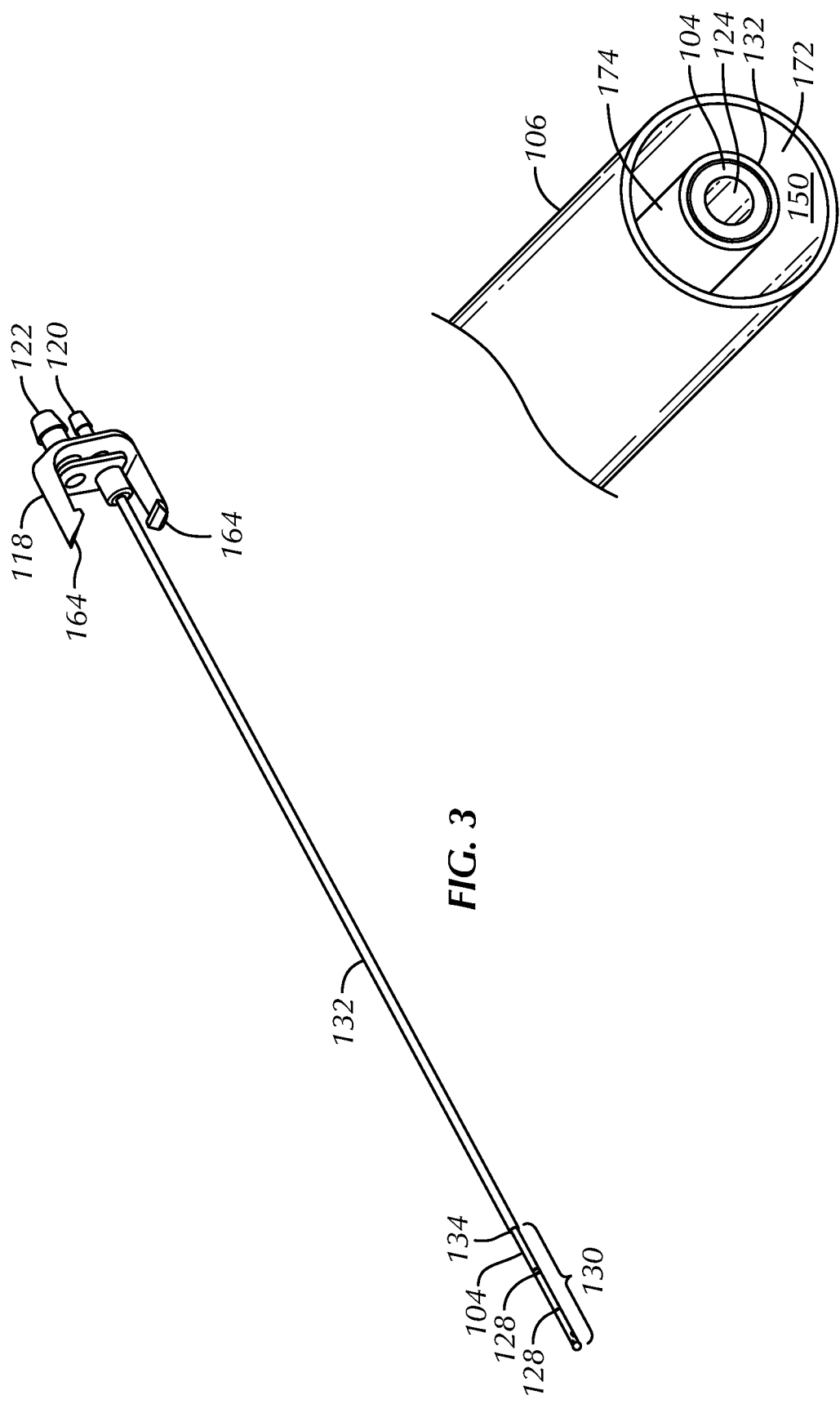

SUCTION AND IRRIGATION DEVICE

RELATED APPLICATION

This Application is a U.S. National Stage filing under 35 U.S.C. § 371 of International Application No. PCT/US2016/029639, filed Apr. 28, 2016, which claims priority to U.S. Provisional Patent Application No. 62/290,882 filed on Feb. 3, 2016, which are hereby incorporated by reference. Priority is claimed pursuant to 35 U.S.C. §§ 119, 371 and any other applicable statute.

TECHNICAL FIELD

The technical field generally relates to devices and methods for irrigating or suctioning fluid from a body lumen or cavity of a mammal such as a human.

BACKGROUND

In recent years, sinus surgeons have improved treatment of nasal and sinus conditions. For example, dilating sinus drainage pathways with balloon catheters has become a new standard of care in treating chronic and acute rhinosinusitis. Sinus surgeons have also begun to treat a broader array of nasal and sinus conditions in the comfort of the physician's office setting and under local anesthesia, rather than operating on those same patients in an operating room setting under general anesthesia.

These changes in sinus treatment have given rise to needs for improved sinus surgery tools.

SUMMARY

The present invention includes articles and methods for irrigating or suctioning fluid from a body lumen or cavity of a mammal (e.g., a human).

In some embodiments, the present invention includes an irrigation and suction device comprising an irrigation tube that defines an irrigation lumen; a suction tube slidably mounted on the irrigation tube, wherein an outer wall of the irrigation tube and an inner wall of the suction tube cooperatively define a suction channel; a handle secured to a proximal portion of the irrigation tube; and a slide member secured to the suction tube and slidably mounted within the handle. Advancing the slide member distally along the handle advances the suction tube along a length of the irrigation tube.

In further embodiments, the present invention includes methods of using the irrigation and suction devices described herein to suction or irrigate a body cavity or lumen of a patient. The methods can include providing an irrigation and suction device according to any of the examples of embodiments described herein, directing the irrigation tube through the nostril of the patient and to a desired location within the body cavity or lumen of the patient, and directing a fluid through the irrigation tube of the device or suctioning fluid through the suction tube of the device.

The present invention provides the devices and tools needed to allow for irrigation and suctioning of fluids within a mammalian body. The devices of the present invention include an irrigation tube that is malleable under the type of forces typically exerted by human fingers, which means a practitioner of the invention can readily shape the irrigation tube to better navigate torturous anatomy without the use of expensive or complicated shaping tools. The devices of the present invention also allow a practitioner to place irrigation spray ports and a suction tube at a desired location of the body with a single hand. That is, a practitioner can guide the irrigation tube and the suction tube to a desired location with a single hand, thereby freeing the user's other hand for other purposes, such as operating other surgical instruments (e.g., an endoscope).

The present invention enables a practitioner to irrigate the ducts, drainage pathways, or any other orifices in a mammalian body (e.g., from the sinus cavities and drainage pathways of a human body) with a fluid, suction or aspirate fluids or small solid particles from the same locations in the body, or both irrigate and suction simultaneously or sequentially from those same locations in the body. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 illustrates a perspective view of an irrigation tube of the present invention.

FIG. 4 which shows a cut-away view along lines A-A of FIG. 1.

DETAILED DESCRIPTION OF THE ILLUSTRATED EMBODIMENTS

The present invention relates to irrigation and suction devices that may be used to irrigate and suction fluid from a lumen or cavity (e.g., a nasal passageway or nasal sinus space).

Figure 1:
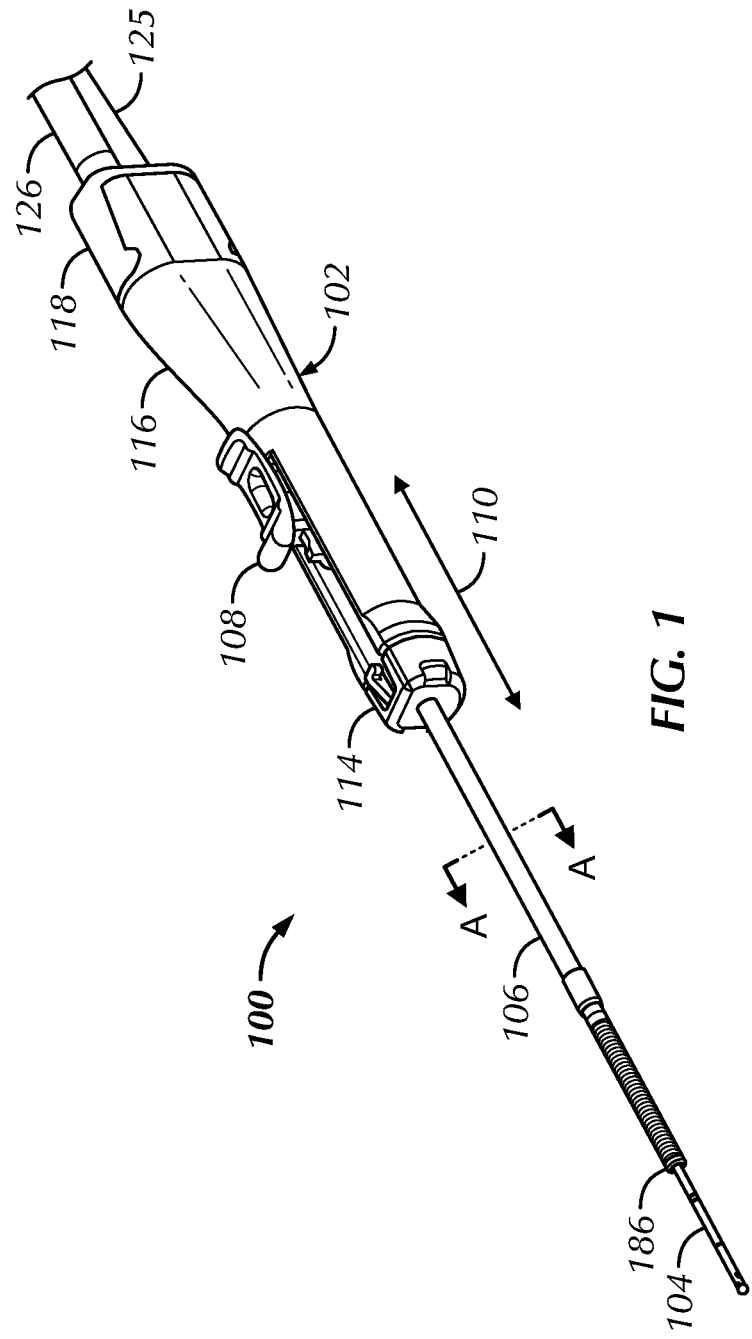
FIG. 1 illustrates a perspective view of one example of an irrigation and suction device of the present invention.
Figure 2:
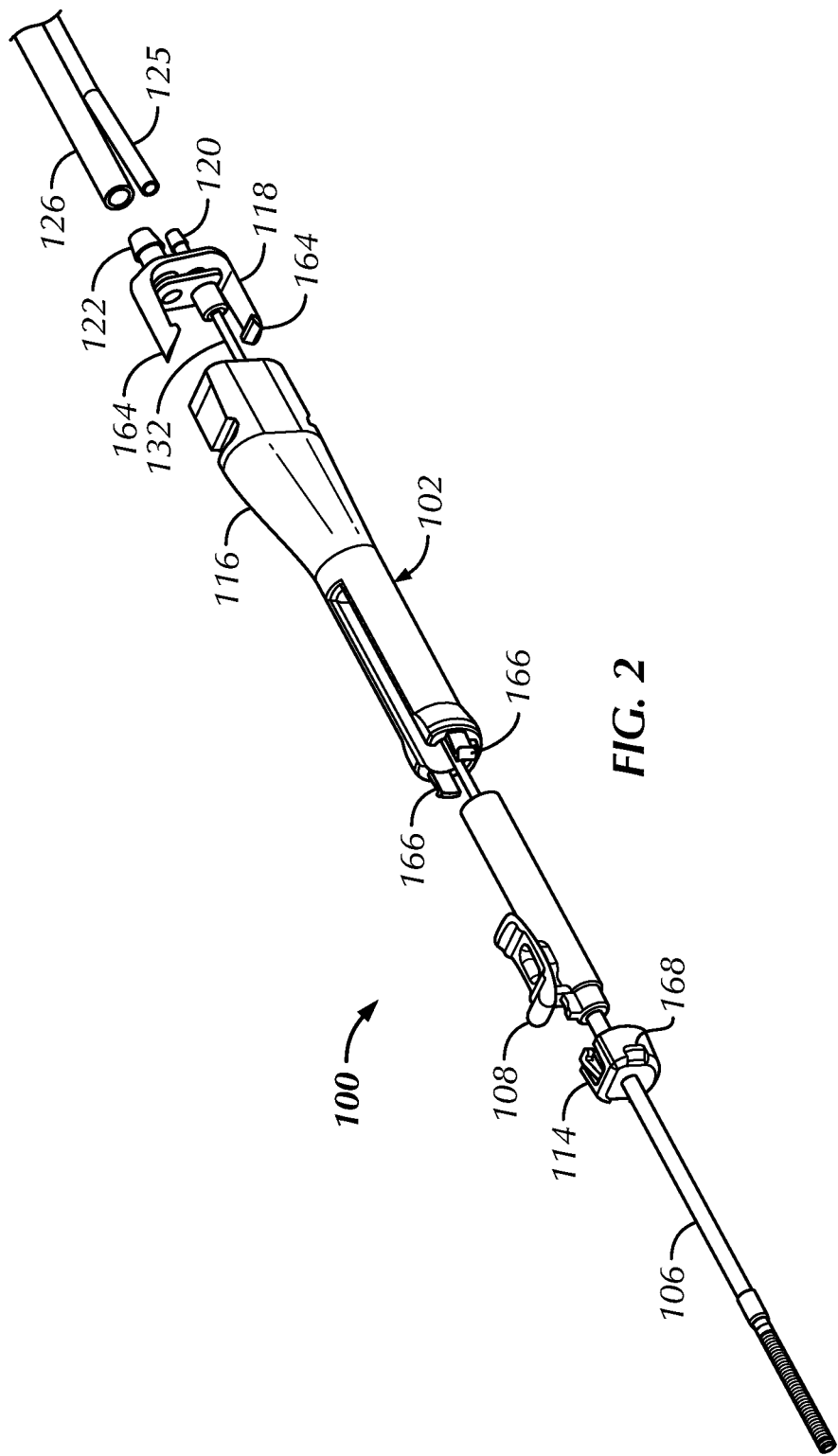
FIG. 2 illustrates an exploded view of the irrigation and suction device shown in FIG. 1.

FIG. 1 illustrates a perspective view of one example of an irrigation and suction device 100 of the invention. The irrigation and suction device 100 includes a handle 102, an irrigation tube 104, a suction tube 106, and a slide member 108. Briefly, and as will be explained in further detail below, a practitioner of the invention can shape the irrigation tube 104 to better access tight anatomical passages, can irrigate anatomical sites with the irrigation tube 104, can suction fluid from an anatomical site with the suction tube 106, and can direct the suction tube 106 along the irrigation tube 104 by moving the slide member 108 in a direction that is parallel to the direction of arrow 110. FIG. 2 illustrates an exploded view of the irrigation and suction device 100.

The handle 102 includes three body components in the form of distal cap 114 (also referred to as a retainer cap), main body 116, and proximal cap 118. The irrigation tube 104 (obscured by other components in FIG. 2) extends through the main body 116 of the handle 102, and a proximal portion of the irrigation tube 104 is secured to the proximal cap 118. A proximal portion of the suction tube 106 is secured to a distal portion of the slide member 108, with the suction tube 106 extending through an orifice defined by the distal cap 114 of the handle 102.

FIG. 3 illustrates a perspective view of the irrigation tube 104 assembled to the proximal cap 118. The proximal cap 118 includes an irrigation port 120 and a suction port 122, which are respectively coupled to an irrigation line 125 and a suction line 126 (not illustrated in FIG. 3, but shown in FIGS. 1 and 2). The irrigation tube 104 is hollow and defines an irrigation lumen extending along the length of the irrigation tube 104. The proximal end of the irrigation tube 104 is secured to the proximal cap 118. The irrigation lumen is in fluid communication with the irrigation port 120 of the proximal cap 118. Two markers 128 are located on the outer surface of the distal portion 130 of the irrigation tube 104. In some embodiments, one or both of markers 128 are radiopaque.

The irrigation tube 104 is made from a material that is sufficiently malleable such that a practitioner of the invention is able to shape the distal portion 130 by hand or with only a small unpowered shaping tool. The irrigation tube may be sized as desired in order to facilitate the use of device 100 in a given part of the anatomy. For example, if the device 100 is to be used in the anatomy of the human nasal cavity, nasal sinuses, or Eustachian tubes, then it may be beneficial for the irrigation tube 104 to be made of a metallic hypotube (e.g., a stainless steel hypotube) having an inner diameter of between about 0.010 inches (~0.254 millimeters) to about 0.050 inches (~1.27 millimeters) and an outer diameter of between about 0.020 inches (~0.508 millimeters) to about 0.080 inches (~2.032 millimeters). In further examples, the irrigation tube 104 may be made of SAE 304 stainless steel having an inner diameter of 0.030 inches (~0.762 millimeters) and an outer diameter of about 0.050 inches (~1.27 millimeters). The distal portion 130 or the entire length of irrigation tube 104 may also be annealed in order to impart the desired degree of malleability.

Optionally, a reinforcing member may be included in the present invention to provide some or all of the length of the irrigation tube 104 with increased stiffness or rigidity. For example, and as best illustrated in FIG. 4 which shows a cut-away view along lines A-A in FIG. 1, a reinforcement member in the form of reinforcement tube 132 is arranged coaxially on the irrigation tube 104. The inner diameter of the reinforcement tube 132 is in contact or in approximate contact with the outer diameter of the irrigation tube 104. As best shown in FIG. 3, the reinforcement tube 132 extends coaxially on the irrigation tube 104 from the proximal end of the irrigation tube 104 within the proximal cap 118 to the distal end 134 of the reinforcement tube 132 at or near the distal portion 130 of the irrigation tube 104. In this way, the reinforcement tube 132 provides for increased stiffness or rigidity along the portion of the irrigation tube 104 that is proximal to distal portion 130, while leaving the distal portion 130 more easily shaped by the hands of the user. While device 100 includes the reinforcing member 132 arranged on the outer side of irrigation tube 104, a reinforcing member could instead, or in addition to, be arranged on the inner wall of the irrigation tube. The proximal end of reinforcement tube 132 may be textured or perforated so as to provide for better attachment of the reinforcement tube 132 to the proximal cap 118.

Figure 5:
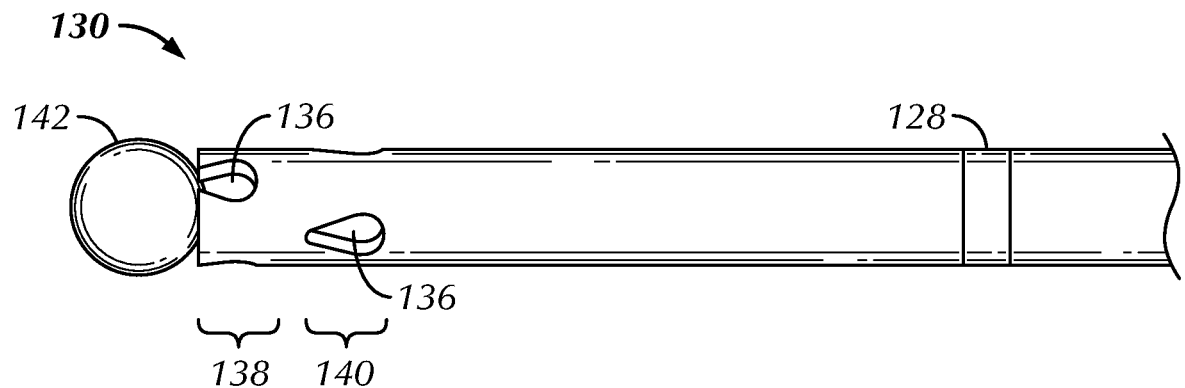
FIG. 5 illustrates a close-up perspective view of a part of a distal portion of an irrigation tube of the present invention.

FIG. 5 illustrates a close-up perspective view of a part of the distal portion 130 of the irrigation tube 104. The distal portion 130 includes a total of six irrigation or spray ports 136, with three of the ports 136 arranged circumferentially in a first band 138 about the irrigation tube 104 and another three of the ports arranged circumferentially in a second band 140 about the irrigation tube 104. The first band 138 of spray ports 136 is located at the very distal end of the irrigation tube 104, while the second band 140 of spray ports 136 is located slightly proximal to the first location. The three ports 136 of each of the first and second bands 138, 140 are arranged in an equidistance manner about the circumference of the irrigation tube 104 (i.e., at 120° intervals), but the ports 136 of the first band 138 are off-set from the portions of the second band 140 in a gauche manner (i.e., the ports of the first band 138 are off-set from those of the second band 140 by about 60°). The ports 136 have a tear-drop shape, with the narrow "tips" of the tear-drop shapes of the ports 136 of the first band 138 slightly truncated at the distal tip of the irrigation tube 104. The tear-drop shape of the ports 136 provide a spray hole geometry that directs spray distally, with the "tail" of the tear-drop shaped holes causing streams of irrigation fluid to deflect forwards. While FIG. 5 illustrates a specific number of tear-dropped spray ports, the present invention is not so limited and the irrigation and suction devices of the present invention may include any number of irrigation ports of any desired shape and arranged in any desired pattern so as to provide an irrigation spray pattern suitable for a given application.

The distal end of the irrigation tube 104 includes an atraumatic tip, in the form of spherical member 142. The atraumatic tip helps prevent or minimize tissue damage while a practitioner navigates a patient's anatomy with the device 100. In alternative embodiments, rather than include a spherical member 142 the distal end of irrigation tube 104 may be rounded so as to provide an atraumatic tip.

Figure 6:
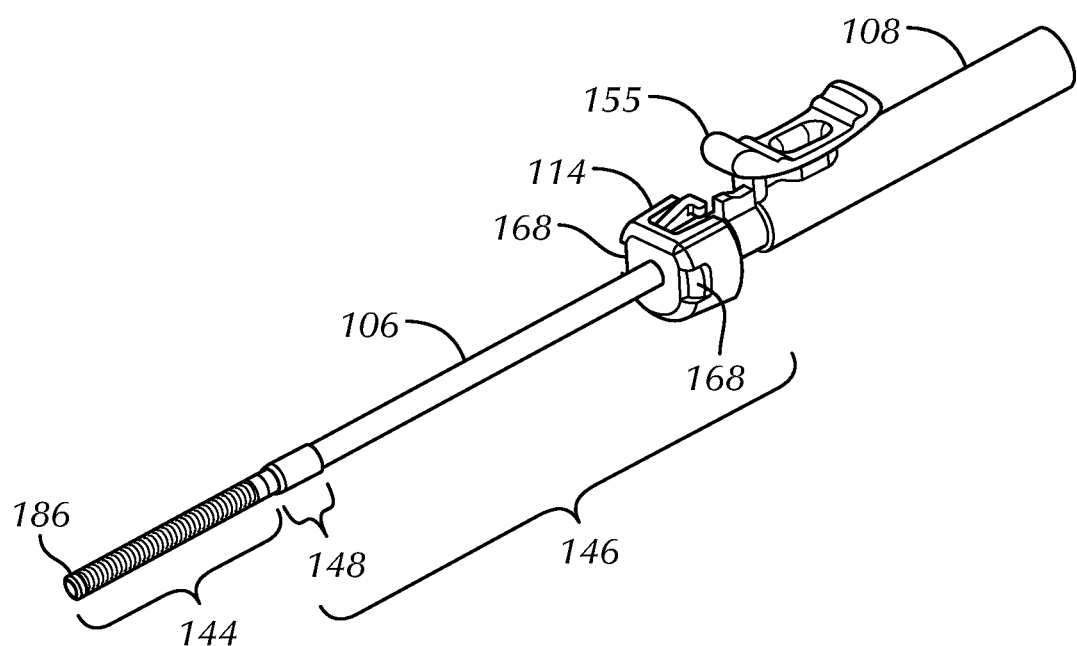
FIG. 6 illustrates a perspective view of a suction tube, a distal cap of a handle, and a slide member, all of the present invention.

FIG. 6 illustrates a perspective view of the suction tube 106, the distal cap 114 of the handle 102, and the slide member 108. The suction tube 106 includes a distal portion 144, a proximal portion 146, and a joinder portion 148. The distal portion 144 can be made from a flexible material, such as a polymeric material or a polymeric material reinforced with embedded mesh or wire (the reinforcement may be accomplished by laser cutting a coil or mesh from a distal portion of the tube used to form proximal portion 146), that readily deforms as the suction tube 106 is tracked over the irrigation tube 104. The proximal portion 146 can be made of a less flexible material (e.g., a stainless steel tube) that provides a desired amount of column or bending strength to the suction tube 106. The joinder portion 148 may be the portion of the suction tube 106 where the flexible material of the distal portion 144 overlaps the less flexible material of the proximal portion 146. For example, the portion of the less flexible material that extends into the joinder portion 148 may be textured (e.g., by grit blasting or laser cutting) so that it more easily adheres or bonds with the flexible material that extends into the joinder portion 148. The distal portion 144 and proximal portion 146 can be secured together at the joinder portion 148 by, for example, laminating the material of the distal portion 144 coaxially over or within the proximal portion 146, use of an adhesive material, reflowing component materials, or interdigitating the proximal portion 146 into or within the distal portion. In some embodiments the flexible material of the distal portion 144 may extend well into or even along the entire length of the proximal portion 146 such that there is no discernable joinder portion 148.

Figure 7:
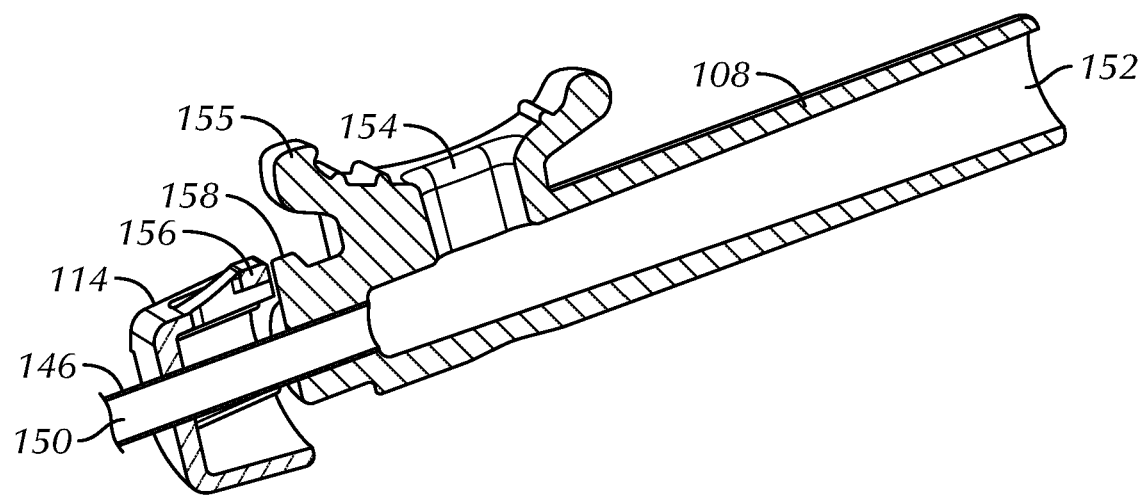
FIG. 7 illustrates a cut-away side-view of a slide member and a proximal portion of a suction tube, both of the present invention.

The proximal portion 146 extends through the distal cap 114 of the handle 102 and is secured to a distal end of the slide member 108. FIG. 7 illustrates a cut-away side-view of the slide member 108 and the proximal portion 146 of the suction tube 106. The slide member 108 defines an interior cavity 152 which is in fluid communication with a suction channel 150. The suction channel 150 is defined by the proximal portion 146 but also extends through the distal portion 144 and the joinder portion 148 of the suction tube 106. The slide member 108 also defines a suction vent 154 and a finger post 155, with the suction vent 154 extending through the middle of the finger post 155 and at a right angle from the longitudinal axis of the main body of the slide member 108. The suction vent 154 is in fluid communication with the cavity 152 and, in turn, the suction channel 150.

The various portions of the suction tube 106 may be sized as desired to facilitate the use of the device 100 in a given part of the anatomy. For example, if the device 100 is to be used in the anatomy of the human nasal cavity, nasal sinuses, or Eustachian tubes, then it may be beneficial for (i) the distal portion 144 to have an inner diameter of between about 0.045 inches (~1.14 millimeters) and about 0.135 inches (~3.43 millimeters) and an outer diameter of between about 0.060 inches (~1.52 millimeters) and about 0.180 inches (~4.57 millimeters), (ii) the joinder portion 148 to have an outer diameter of between about 0.100 inches (~2.54 millimeters) and about 0.200 inches (~5.08 millimeters), and (iii) the proximal portion to have an inner diameter of between about 0.060 inches (~1.52 millimeters) and about 0.180 inches (~4.57 millimeters) and an outer diameter of between 0.070 inches (~1.78 millimeters) and about 0.190 inches (~4.83 millimeters). In further examples, the distal portion may have an inner diameter of about 0.091 inches (~2.31 millimeters) and an outer diameter of about 0.120 inches (~3.05 millimeters), the joinder portion may have an outer diameter of about 0.150 inches (~3.81 millimeters), and the proximal portion may have an inner diameter of about 0.122 inches (~3.10 millimeters) and an outer diameter of about 0.134 inches (~3.40 millimeters). In some embodiments, the inner diameter of the proximal portion 146 is larger or smaller than the inner diameter of the distal portion 144. Also, the outer diameter of the proximal portion 146 may be larger or smaller than the outer diameter of the distal portion 144. It can, for example, be useful for the proximal portion 146 to have a larger inner diameter than the distal portion 144 so as to decrease the likelihood that the proximal portion 146 will become clogged by fluid or solids aspirated during use. In another example, it may be useful for the proximal portion 146 to have a larger outer diameter than the distal portion 144 so that the distal portion 144 can be more easily advanced into body lumens.

FIG. 7 also illustrates a side-view of a forward stop 156 and a distal prong 158. As will be explained in further detail below, the distal prong 158 is a portion of the slide member 108 that is configured to resistantly engage the forward stop 156 of the distal cap 114.

Figure 8:
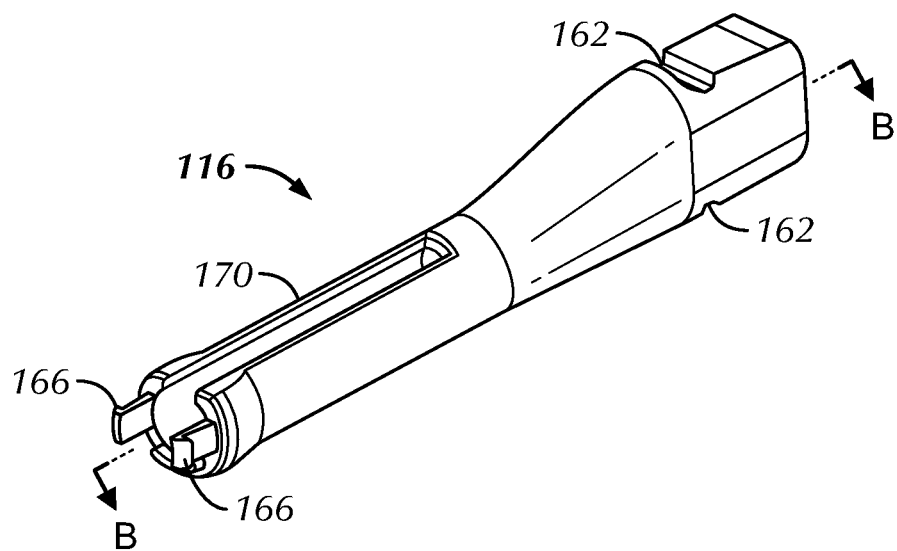
FIG. 8 illustrates a perspective view of a main body of a handle of the present invention.
Figure 9:
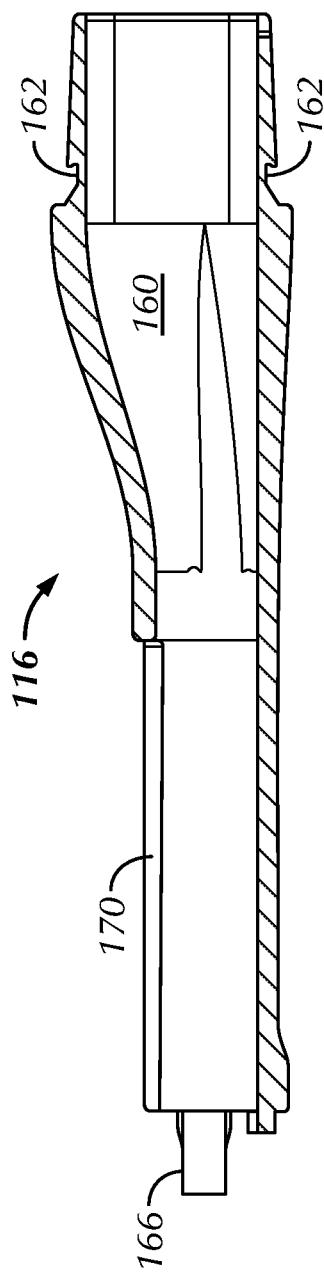
FIG. 9 illustrates a cut-away side view of a main body of a handle of the present invention taken along the line B-B of FIG. 8.

FIG. 8 illustrates a perspective view of the main body 116 of the handle 102, while FIG. 9 illustrates a cut-away side view. The proximal end of the main body 116 includes two detents 162 that engage two complimentary prongs 164 (illustrated in FIG. 2 or 3) of the proximal cap 118. The prongs 164 cooperate with the two detents 162 to provide a snap-fit between the main body 116 and the proximal cap 118. The distal end of the main body 116 includes two prongs 166 that cooperate with two detents 168 (illustrated in FIG. 2 or 6) defined in the distal cap 114, thereby securing the distal cap 114 to the main body 116. The main body 116 also defines a slot 170, which runs down a portion of the longitudinal length of the main body 116. As will be explained further below, the slot 170 provides a defined track in which the slide member 108 may translate. The main body 116 also defines a suction chamber 160 (illustrated in FIG. 9).

Figure 10:
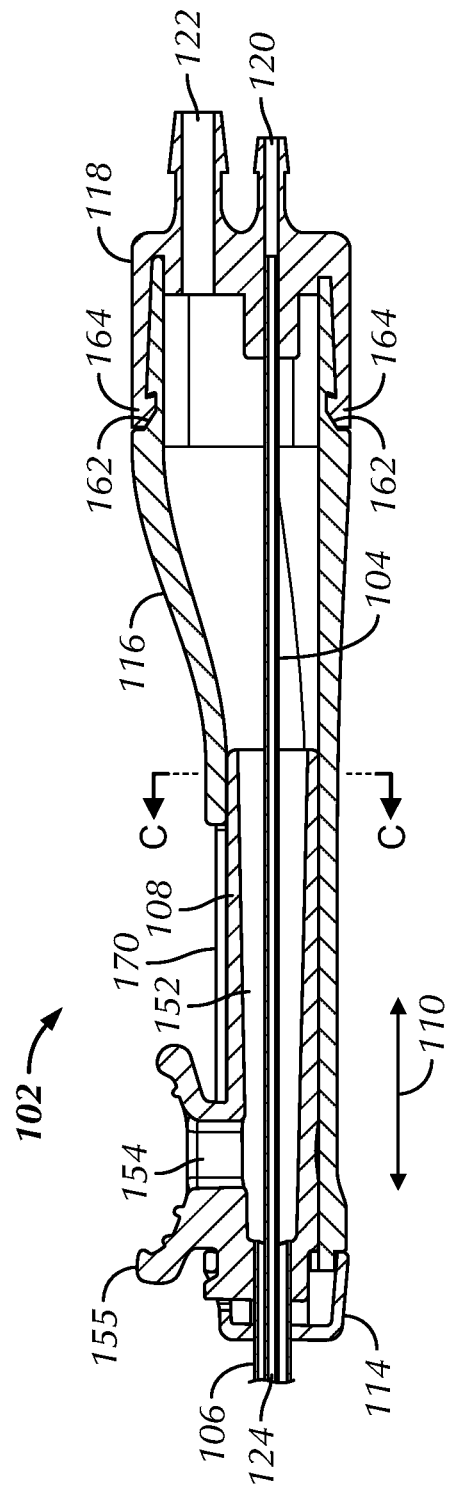
FIG. 10 illustrates a cut-away side view of a handle of the present invention.

FIG. 10 illustrates a cut-away side view of the handle 102 fully assembled to the suction tube 106 and irrigation tube 104. The proximal end of the irrigation tube 104 is secured within the lumen of the irrigation port 120 of the proximal cap 118. Together, the irrigation tube 104 and the irrigation port 120 define an irrigation lumen 124 that extends from the irrigation port 120 to the spray ports 136. The proximal end of the suction tube 106 is secured within the lumen of the slide member 108. The slide member 108 is moveably constrained within the main body 116 of the handle 102, with the finger post 155 extending through the slot 170. The slide member 108 may translate along slot 170 along a direction that is parallel with the direction of arrow 110.

The handle 102 defines a suction chamber 160 that is in fluid communication with the suction port 122, the cavity 152 of the slide member 108, and the suction channel 150 of the suction tube 106. As perhaps best illustrated in FIG. 4, the suction channel 150 extends down the length of the suction tube 106 in the annular space defined between the inner wall 172 of the suction tube 106 and the outer wall 174 of the reinforcement tube 132 (or between the inner wall of the suction tube 106 and the outer wall of the irrigation tube 104 if a reinforcement tube is not utilized). The suction channel 150 can have an annular cross-sectional area—i.e., the area in the annular space lying between the inner wall 172 of the suction tube and the outer wall 174 of the reinforcement tube (or the outer wall of the irrigation tube 104 if no reinforcement tube is present)—of any size needed to provide a desired amount of suction. For example, the suction channel 150 may have an annular cross-sectional area of between about 0.001 square inches (~0.645 square millimeters) to about 0.126 square inches (~81.3 square millimeters). In a further example, the suction channel 150 may have an annular cross-sectional area of between about 0.013 square inches (~8.39 square millimeters) to about 0.038 square inches (~24.5 square millimeters). In a further example, the suction channel 150 may have an annular cross-sectional area of about 0.025 square inches (~16.1 square millimeters).

Figure 11:
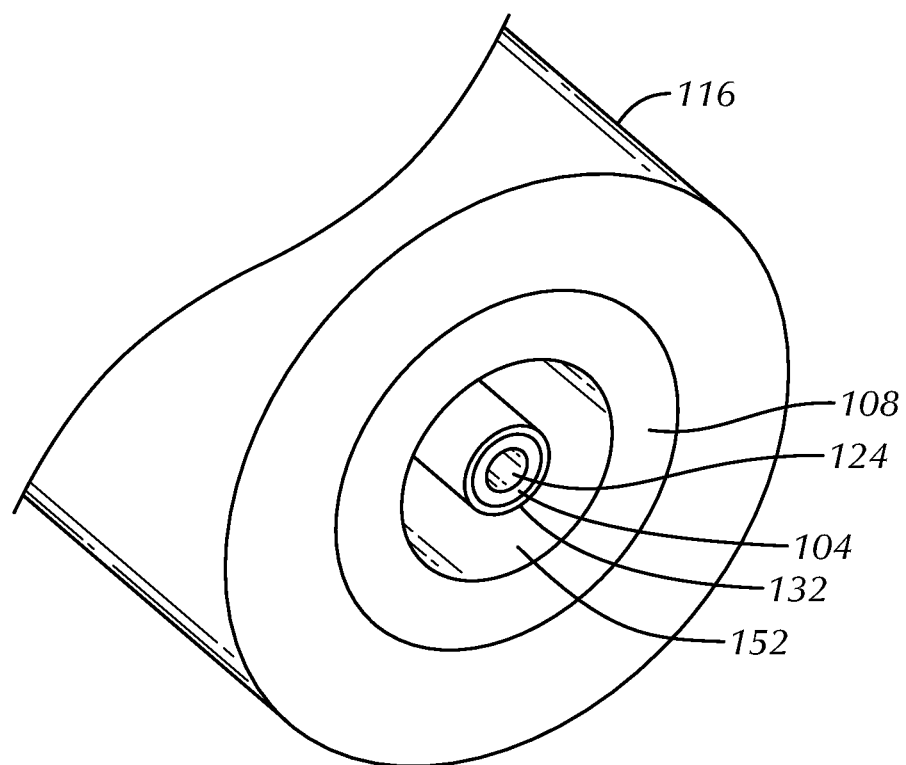
FIG. 11 illustrates a cut-away view showing a radial profile of a handle of the present invention.

FIG. 11 illustrates a cut-away view of the radial profile of the device 100 along lines C-C in FIG. 10. The slide member 108 is arranged within the handle 116 with a relatively small clearance therebetween so that a tight fit is formed between the slide member 108 and inner wall of the handle 116. This tight fit prevents an undesirable breach of the low pressure environment within the suction chamber 160 when a suction source is applied to the suction port 122. The cavity 152 is defined between the inner wall of the slide member 108 and the outer wall of the reinforcement tube 132. The irrigation tube 104 is positioned within and against the inner wall of the reinforcement tube 132. The irrigation lumen 124 is defined within the irrigation tube 104.

Figure 12:
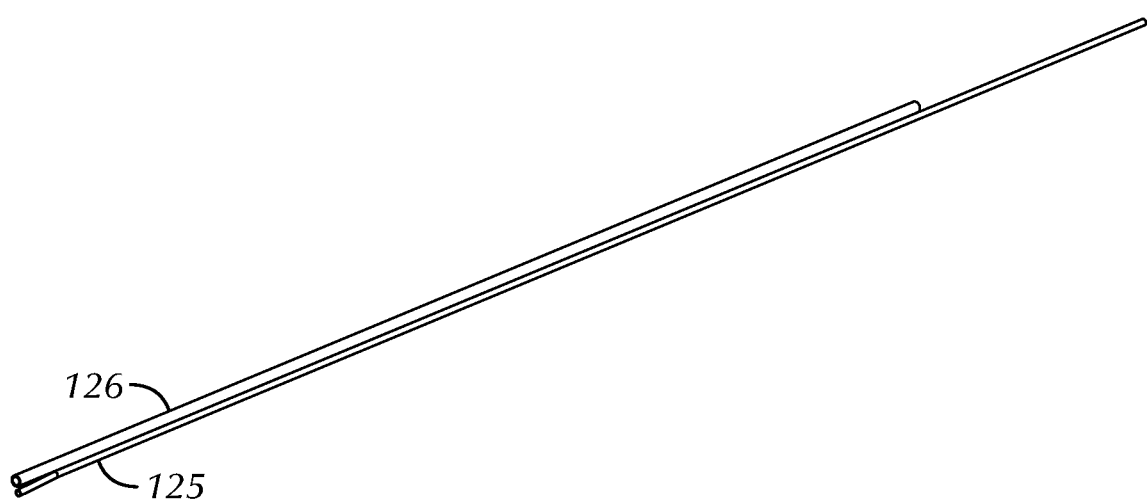
FIG. 12 illustrates a perspective view of an irrigation line and suction line of the present invention.

FIG. 12 illustrates a perspective view of the irrigation line 125 and suction line 126. The irrigation line 125 can be secured to the irrigation port 120 while the suction line 126 may be secured to the suction port 122. The irrigation line 125 and suction line 126 may be weakly adhered together such that a practitioner of the invention may delaminate one from the other during use.

Figure 13:
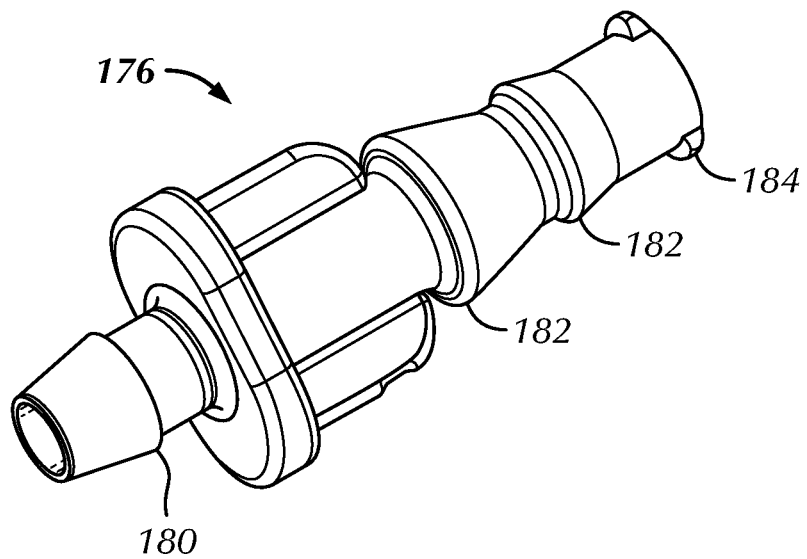
FIG. 13 illustrates an adapter of the present invention.
Figure 14:
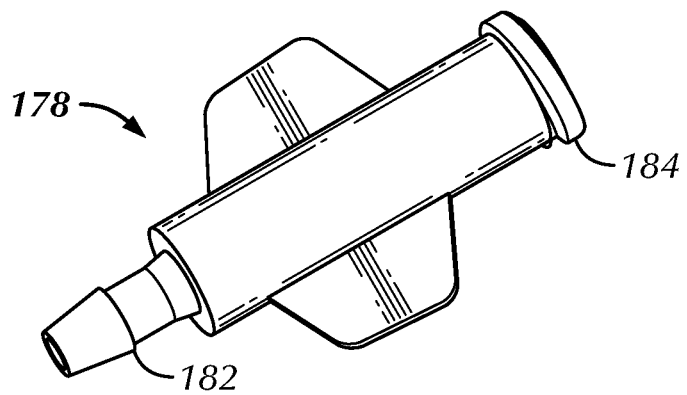
FIG. 14 illustrates an adapter of the present invention.

FIG. 13 illustrates an adapter 176 for use with the irrigation line 125 or suction line 126. Adapter 176 includes a barb fitting 180 on one side and two barb fittings 182 on the opposite side. Adapter 176 also includes a female Luer-type fitting 184. The combination of the barb fitting 180, the barb fittings 182, and the Luer-type fitting 184 provides adapter 176 with the versatility to connect the irrigation and suction lines 125, 126 with a wide variety of different suction and fluid sources. Alternative adapter designs are also encompassed by the present invention, such as the adapter 178 illustrated in FIG. 14 which includes one end with a barb 182 fitting and the opposite end with a Luer-type fitting 184.

During use of the irrigation and suction device 100, a practitioner of the invention can connect a fluid source (e.g., water, saline, active bacterial culture, or a drug solution) to the device 100 at either the irrigation port 120 or to the proximal end of the irrigation line 125. The practitioner can bend or manipulate the distal portion 130 of the irrigation tube 104 to place it into a shape that is more advantageous for negotiating the contours of the anatomy to place the distal tip of the irrigation tube 104 at the desired location within a body lumen or cavity. While holding the handle 102 with a hand, the practitioner can direct the distal tip of the irrigation tube 104 to the desired location. Once placed at the desired location, the practitioner can direct the fluid through the irrigation line 125 (if used), through the irrigation port 120, through the irrigation lumen 124 and out of the spray ports 136 at the distal end of the irrigation tube 104. In this way, the practitioner can use device 100 to access and irrigate the desired location with a patient's anatomy. The patient may be, for example, a human or other mammal.

The practitioner can also use the device 100 to suction fluid (e.g., blood, saliva, mucus, other body fluids, the fluid directed through the irrigation lumen 124, or mixtures thereof) at or near the desired location. To accomplish this, the practitioner connects a suction source to the barb or Luer fitting of adapters 176 or 178, to the proximal end of the suction line 126, or to the suction port 122. Since the suction channel 150, cavity 152, suction chamber 160, and suction port 122 are all in fluid communication, attaching the suction source will create a vacuum that extends through each of those regions and provides a suction force at the distal tip 186 of the distal portion 144 of the suction tube 106 as well as at the suction vent 154 of the slide member 108. When a practitioner blocks the suction vent 154, by, for example, placing a finger on the finger post 155 in a way that obstructs the suction vent 154, it increases the suction force at the distal tip 186. Any fluids that come close to the distal tip 186 will be drawn by the suction force into the suction channel 150, through the device 100, and out of the suction port 122 or proximal end of the suction line 126. If the practitioner clears the block from the suction vent 154, by, for example, removing his/her finger from obstructing the suction vent 154, then the suction force at the distal tip 186 will diminish.

The practitioner may also irrigate anatomy with the irrigation fluid while simultaneously suctioning all or some of the irrigation fluid from the anatomy. This can be useful to prevent the anatomy from becoming "flooded" with irrigation fluid. The flow path of the irrigation fluid (e.g., the irrigation lumen 124 and/or spray ports 136) and the return paths of the suction effluent (e.g., the suction channel 150) may be sized such that the device's suction rate is 0.1 to 10 times that of its irrigation rate; namely, when fully engaged, the suction rate of the device may be between 0.1 and 10 times that of the irrigation rate of the device. In further embodiments, the suction rate of the device may be between 1 and 4 times that of the irrigation rate of the device. In some embodiments the suction rate of the device is twice as large as the irrigation rate. In further embodiments, the suction rate of the device is between 2 and 4 times as large as the irrigation rate.

The practitioner can also translate or move the position of the distal tip 186 along the irrigation tube 104 by using a finger to translate the slide member 108 using the finger post 155 along the slot 170 in the main body 116 of the handle 102.

Figure 15:
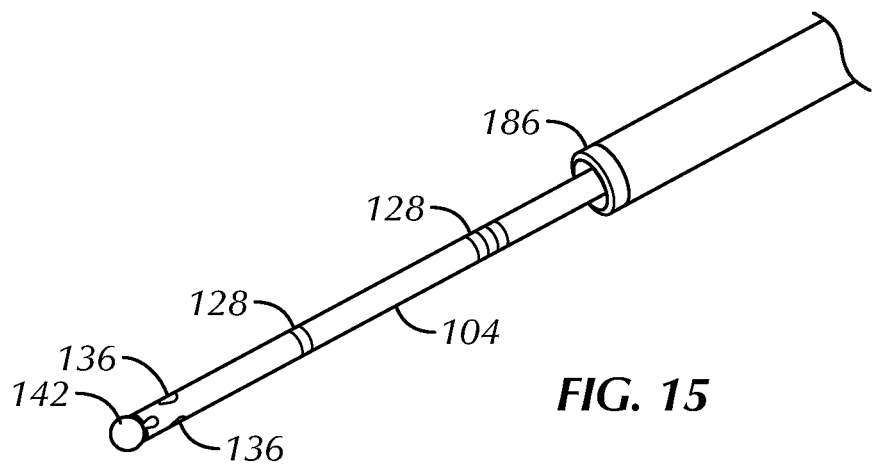
FIG. 15 illustrates a perspective view of a distal portion of an irrigation tube of the present invention.

FIG. 1 illustrates the device 100 in a state where the slide member 108 is fully retracted or pulled proximally within the slot 170. FIG. 15 illustrates a perspective view of a distal portion of the irrigation tube 104 showing the relative position of the distal tip 186 when the slide member 108 is pulled fully proximally within the slot 170. The distal tip 186 (and any suction force that may be applied there) is fully pulled back from the position of the irrigation ports 136. The markers 128 are fully exposed. In this position, most of the fluid ejected from the irrigation ports 136 will not be immediately suctioned up at the distal tip 186 but will instead have a relatively long time to contact and irrigate the desired anatomical locations.

Figure 16:
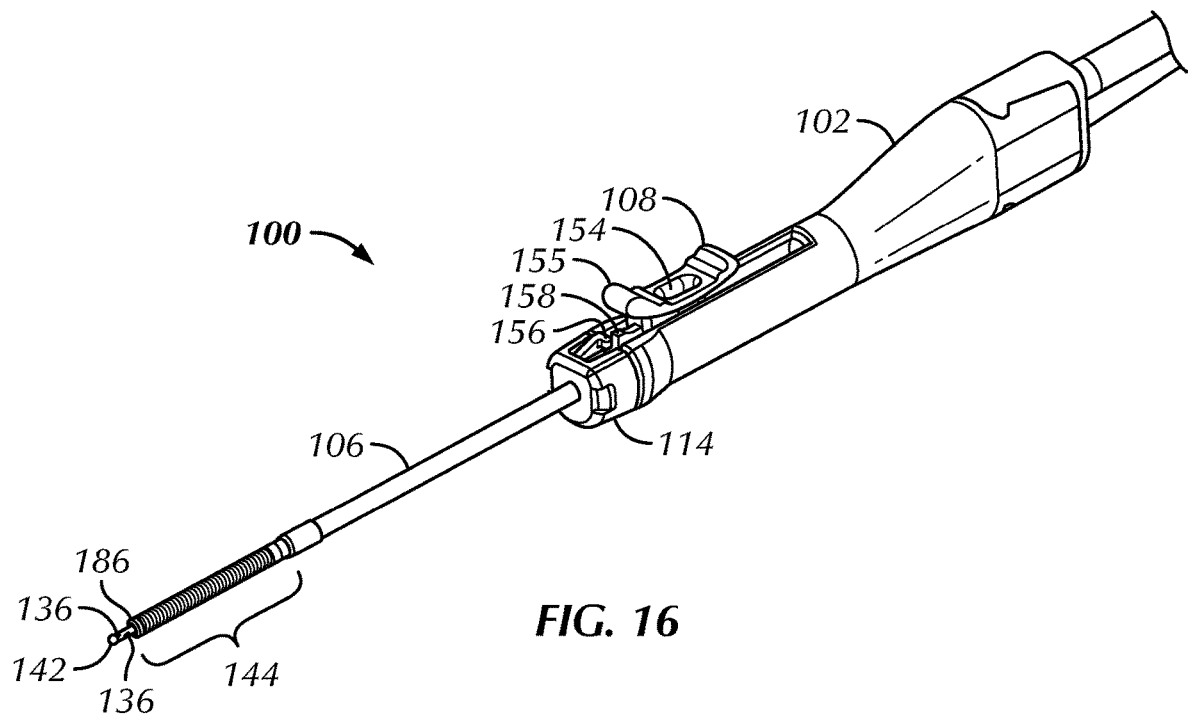
FIG. 16 illustrates a perspective view of the irrigation and suction device of the present invention.

FIG. 16 illustrates the device 100 in a state where the slide member 108 has been extended or advanced distally within the slot 170 to the point where the distal prong 158 of the slide member 108 has made contact with the forward stop 156 on the distal cap 114 of the handle 102. At this position, the distal tip 186 has been advanced distally along the irrigation tube 104 to a position that is at or just proximal to the irrigation ports 136. The distal portion 144 of the suction tube 106 now overlies the markers 128. In this position, the distal tip 186 can be used to quickly suction up most of the irrigation fluid ejected from the irrigation ports 136 when a finger is held over the suction vent 154, thereby reducing the likelihood that an undesirable amount of irrigation fluid will build up at the irrigation spot within the patient's anatomy.

When advanced to the position shown in FIG. 16, the distal prong 158 of the slide member 108 is pressed against the forward stop 156 of the distal cap 114 of the handle 102.

Figure 17:
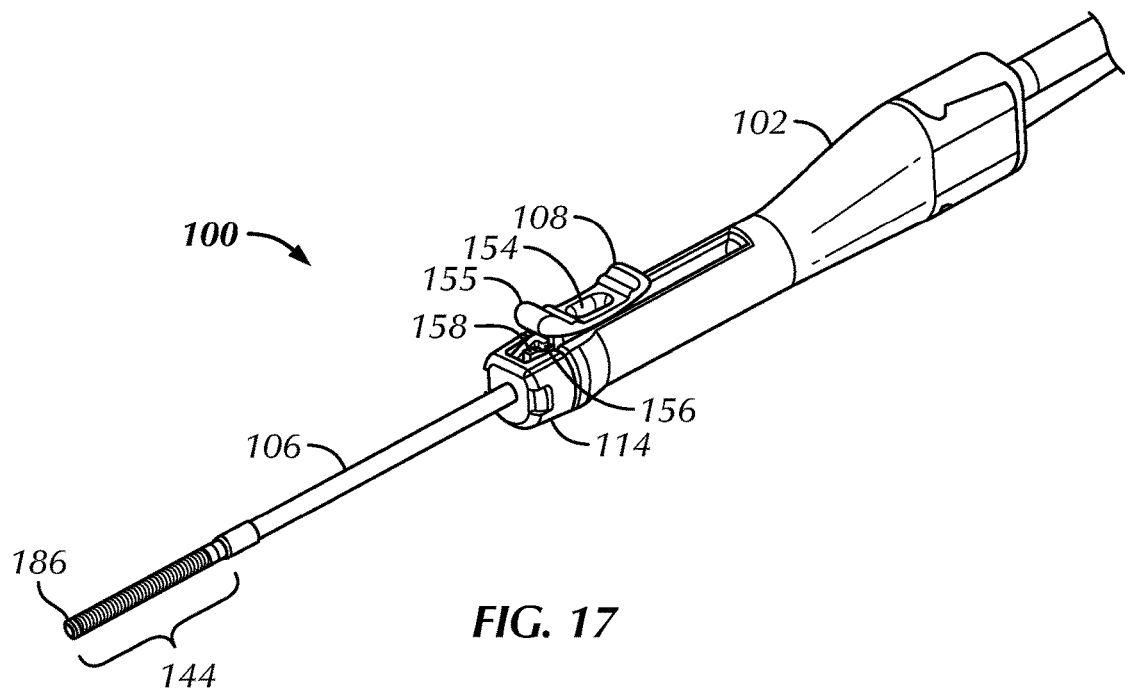
FIG. 17 illustrates a perspective view of the irrigation and suction device of the present invention.

If the practitioner presses firmly, he/she can force the distal prong 158 past the forward stop 156 to advance the distal tip 186 of the suction tube 106 further distally along the irrigation tube 104. FIG. 17 illustrates the device 100 when the slide member 108 has been fully advanced distally such that the distal prong 158 of the slide member 108 has been forced past the forward stop 156 of the distal cap 114, thereby placing the distal tip 186 of the suction tube 106 distally past or adjacent to the spherical member 142 of the irrigation tube 104. In this way, the forward stop 156 and distal prong 158 provide tactile "force feedback" to the practitioner such that he/she can readily tell if the distal tip 186 of the suction tube 106 is at or proximally adjacent to the irrigation ports 136 or whether the suction tube 106 has been advanced so far that all of the irrigation tube 104 is contained within the suction tube 106. In the fully advanced position shown in FIG. 17, the entire irrigation tube 104 is contained within the suction tube 106. In this position, most or all of any irrigation fluid ejected from the irrigation ports 136 will be aspirated by the distal tip 186 of the suction tube 106 when a finger is held over the suction vent 154 and device 100 may be used in a manner similar to a simple suction device.

Figure 18:
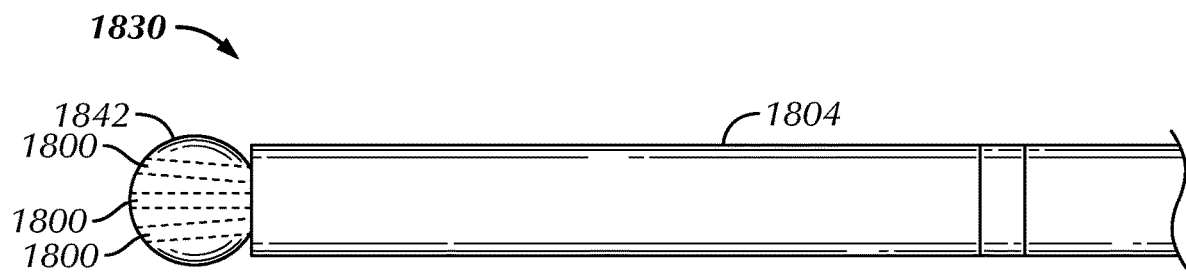
FIG. 18 illustrates a close-up perspective view of a part of a distal portion of an irrigation tube that includes a plurality of forward-facing spray ports in the form of spray channels.

In some embodiments, the irrigation and suction device of the present invention includes irrigation spray channels that provide a more forward-facing spray pattern than what might be achieved by only directing irrigation fluid through the ports 136 of the embodiment illustrated in FIG. 5. For example, FIG. 18 illustrates a close-up perspective view of a part of a distal portion 1830 of an irrigation tube 1804 that includes a plurality of forward-facing spray ports in the form of spray channels 1800. Three spray channels 1800 extend through, and are entirely defined by, spherical member 1842. The spray channels 1800 are in fluid communication with the irrigation lumen extending within the irrigation tube 1804.

Figure 19:
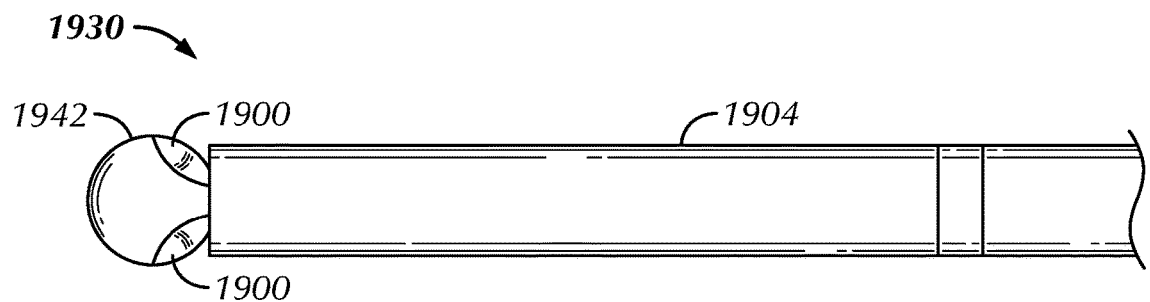
FIG. 19 illustrate a close-up perspective view of another embodiment where the spherical member is not a complete sphere but has instead one or more portions of its outer surface skived or otherwise removed in order to define spray ports in the form of spray channels.

FIG. 19 illustrate a close-up perspective view of another embodiment where the spherical member 1942 is not a compete sphere but has instead has had one or more portions of its outer surface skived or otherwise removed in order to define spray ports in the form of spray channels 1900. Like the spray channels 1800 shown in FIG. 18, the spray channels 1900 shown in FIG. 19 form a flow path for irrigation fluid but the flow path only passes along an outer surface of the spherical member 1942 instead of completely through the spherical member 1942. As such, only a portion of the spray channels 1900 are defined by the spherical member 1942. The spray channels 1900 may be useful for projecting a spray of irrigation fluid out of the side of the distal end of the irrigation tube 1904.

In some embodiments, the irrigation and suction device of the present invention includes two or three of: i) spray ports formed in distal portion of an irrigation tube 104, as illustrated in FIG. 5, ii) spray ports that pass through the atraumatic tip, as illustrated in FIG. 18, and iii) spray ports that pass along an outer surface of an atraumatic tip member, such as the spray channels 1900 that pass along the outer surface of spherical member 2042 shown in FIG. 19. By including two or more different kinds of spray ports in a single device, the irrigation and suction device of the present invention may provide a desired spray pattern of irrigation fluid.

The following are some non-limiting enumerated examples of the invention:

Example 1

The invention includes an irrigation and suction device comprising:

an irrigation tube that defines an irrigation lumen; a suction tube slidably mounted on the irrigation tube, wherein an outer wall of the irrigation tube and an inner wall of the suction tube cooperatively define a suction channel;

a handle secured to a proximal portion of the irrigation tube; and a slide member secured to the suction tube and slidably mounted within the handle, wherein advancing the slide member distally along the handle advances the suction tube along a length of the irrigation tube.

Example 2

The invention of Example 1, wherein a distal portion of the irrigation tube is malleable under forces commonly produced by human fingers.

Example 3

The invention of any one of the above enumerated Examples, wherein the suction tube is coaxially mounted upon the irrigation tube.

Example 4

The invention of any one of the above enumerated Examples, wherein the irrigation tube has an outer diameter of between 0.508 millimeters and 2.032 millimeters.

Example 5

The invention of any one of the above enumerated Examples, wherein the irrigation tube has an inner diameter of between 0.254 millimeters and 1.27 millimeters.

Example 6

The invention of any one of the above enumerated Examples, wherein the suction tube has an inner diameter of between 1.14 millimeters and 4.57 millimeters.

Example 7

The invention of any one of the above enumerated Examples, wherein the suction tube has an outer diameter of between 1.52 millimeters and 5.05 millimeters.

Example 8

The invention of any one of the above enumerated Examples, wherein the suction channel has an annular cross-sectional area of between 0.645 square millimeters and about 81.3 square millimeters.

Example 9

The invention of any one of the above enumerated Examples, wherein a distal portion of the irrigation tube defines a plurality of spray ports in fluid communication with the irrigation lumen.

Example 10

The invention of Example 9, wherein at least some of the spray ports have a teardrop shape.

Example 11

The invention of Examples 9 or 10, wherein at least some of the spray ports are defined at least in part by an atraumatic tip secured to a distal end of the irrigation tube.

Example 12

The invention of Example 11, wherein the atraumatic tip includes a spherical member secured to the distal end of the irrigation tube.

Example 13

The invention of Example 11, wherein the atraumatic tip includes a cone-shaped member secured to the distal end of the irrigation tube.

Example 14

The invention of Example 11, wherein the atraumatic tip defines spray ports that extend completely through the atraumatic tip, spray ports that extend along a surface of the atraumatic tip, spray ports that extend through the irrigation tube, or any combination thereof.

Example 15

The invention of any one of the above enumerated Examples, wherein the device includes a forward stop configured to resist distal advancement of the slide member relative to the handle and wherein advancing the slide member to the forward stop positions a distal tip of the suction tube proximal and adjacent to a distal tip of the irrigation tube.

Example 16

The invention of Example 15, wherein advancing the slide member distally past the forward stop pushes the distal tip of the suction tube distally past the distal tip of the irrigation tube.

Example 17

The invention of any one of the above enumerated Examples, wherein the suction tube is coaxially mounted on the irrigation tube.

Example 18

The invention of any one of the above enumerated Examples, wherein the slide member defines a suction vent, wherein the suction vent is in fluid communication with the suction channel.

Example 19

The invention of any one of the above enumerated Examples, wherein the handle includes a proximal cap secured to the proximal end of the handle.

Example 20

The invention of any one of the above enumerated Examples, wherein the handle defines a suction chamber in fluid communication with a proximal end of the suction channel and wherein the handle includes a suction port and an irrigation port, wherein the suction port is in fluid communication with the suction chamber and the irrigation port is in fluid communication with the irrigation lumen.

Example 21

The invention includes a method of irrigating a body cavity or lumen of a patient, the method comprising:
providing an irrigation and suction device according to any of the above enumerated Examples;
directing the irrigation tube through the nostril of the patient and to a desired location within the body cavity or lumen of the patient; and
directing a fluid through the irrigation tube of the device or suctioning fluid through the suction tube of the device.

Example 22

The invention of Example 21, further including shaping a distal portion of the irrigation lumen prior to directing the irrigation tube through the nostril of the patient.

Example 23

The invention of any one of Examples 21 or 22, further including suctioning fluid from or near the desired location with the suction tube.

Example 24

The invention of any one of Examples 21 to 23, further including holding the handle with a single hand while directing the irrigation tube to the desired location.

Example 25

The invention of any one of Examples 21-24, further including using a finger of the hand grasping the handle to push the slide member distally along the handle.

Example 26

The invention of Example 25, wherein the finger pushes the slide member distally along the handle after the irrigation tube is directed to the desired location.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. It shall be understood that any numerical ranges explicitly disclosed in this document shall include any subset of the explicitly disclosed range as if such subset ranges were also explicitly disclosed; for example, a disclosed range of 1-96.7 shall also include the ranges 1-80.3, 2-76, or any other numerical range that falls between 1 and 96.7.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

While embodiments of the present invention have been shown and described, various modifications may be made without departing from the scope of the present invention. The invention, therefore, should not be limited except to the following claims and their equivalents.

What is claimed is:

1. An irrigation and suction device for irrigating and suctioning fluid from a body lumen or a body cavity of a patient comprising:
   an irrigation tube that defines an irrigation lumen;
   a suction tube slidably mounted on the irrigation tube, wherein an outer wall of the irrigation tube and an inner wall of the suction tube cooperatively define a suction channel, wherein a distal tip of the suction tube and the outer wall of the irrigation tube define an aperture for receiving the fluid into the suction channel from the body lumen or the body cavity;
   a handle coupled to a proximal portion of the irrigation tube; and
   a slide member slidably mounted within the handle,
   wherein the slide member is coupled to the suction tube such that advancing the slide member along the handle advances a distal tip of the suction tube along a length of the irrigation tube,
   wherein the distal tip of the suction tube is movable between a distal position and a proximal position relative to the irrigation tube,
   wherein, at all positions of the distal tip of the suction tube between the distal position and the proximal position, the handle is configured to fluidly couple the suction channel to a suction source, and
   wherein, at all positions of the distal tip of the suction tube between the distal position and the proximal position, the irrigation tube is configured to irrigate the body lumen or the body cavity with a fluid.

2. The device of claim 1, wherein a distal portion of the irrigation tube is malleable under forces commonly produced by human fingers.

3. The device of claim 1, wherein the suction tube is coaxially mounted upon the irrigation tube.

4. The device of claim 1, wherein the irrigation tube has an outer diameter of between 0.508 millimeters and 2.032 millimeters.

5. The device of claim 1, wherein the irrigation tube has an inner diameter of between 0.254 millimeters and 1.27 millimeters.

6. The device of claim 1, wherein the suction tube has an inner diameter of between 1.14 millimeters and 4.57 millimeters.

7. The device of claim 1, wherein the suction tube has an outer diameter of between 1.52 millimeters and 5.05 millimeters.

8. The device of claim 1, wherein the suction channel has an annular cross-sectional area of between 0.645 square millimeters and about 81.3 square millimeters.

9. The device of claim 1, wherein a distal portion of the irrigation tube defines a plurality of spray ports in fluid communication with the irrigation lumen.

10. The device of claim 9, wherein at least some of the spray ports have a teardrop shape.

11. The device of claim 10, wherein at least some of the spray ports are defined at least in part by an atraumatic tip secured to a distal end of the irrigation tube.

12. The device of claim 11, wherein the atraumatic tip includes a spherical member secured to the distal end of the irrigation tube.

13. The device of claim 11, wherein the atraumatic tip includes a cone-shaped member secured to the distal end of the irrigation tube.

14. The device of claim 1, wherein the device includes a forward stop configured to resist distal advancement of the slide member relative to the handle and wherein advancing the slide member to the forward stop positions a distal tip of the suction tube proximal and adjacent to a distal tip of the irrigation tube.

15. The device of claim 14, wherein advancing the slide member distally past the forward stop pushes the distal tip of the suction tube distally past the distal tip of the irrigation tube.

16. The device of claim 1, wherein the slide member defines a suction vent, wherein the suction vent is in fluid communication with the suction channel.

17. The device of claim 1, wherein the handle includes a proximal cap secured to a proximal end of the handle.

18. The device of claim 1, wherein the handle defines a suction chamber in fluid communication with a proximal end of the suction channel and wherein the handle includes a suction port and an irrigation port, wherein the suction port is in fluid communication with the suction chamber and the irrigation port is in fluid communication with the irrigation lumen.

19. A method of irrigating a body cavity or a body lumen of a patient, the method comprising:
providing an irrigation and suction device comprising:
an irrigation tube that defines an irrigation lumen,
a suction tube slidably mounted on the irrigation tube, wherein an outer wall of the irrigation tube and an inner wall of the suction tube cooperatively define a suction channel, wherein a distal tip of the suction tube and the outer wall of the irrigation tube define an aperture for receiving a fluid into the suction channel from the body lumen or the body cavity,
a handle coupled to a proximal portion of the irrigation tube, and
a slide member slidably mounted within the handle,
wherein the slide member is coupled to the suction tube such that advancing the slide member distally along the handle advances a distal tip of the suction tube along a length of the irrigation tube,
wherein the distal tip of the suction tube is movable between a distal position and a proximal position relative to the irrigation tube,
wherein, at all positions of the distal tip of the suction tube between the distal position and the proximal position, the handle is configured to fluidly couple the suction channel to a suction source, and
wherein, at all positions of the distal tip of the suction tube between the distal position and the proximal position, the irrigation tube is configured to irrigate the body lumen or the body cavity with the fluid;
directing the irrigation tube through a nostril of the patient and to a desired location within the body cavity or lumen of the patient;
directing the fluid through the irrigation tube of the device; and
suctioning, from the body cavity or lumen of the patient, the fluid through the suction tube of the device.

20. The method of claim 19, wherein the fluid is directed through the irrigation tube while fluid is suctioned through the suction tube of the device.

21. The method of claim 19, wherein the slide member defines a suction vent, wherein the suction vent is in fluid communication with the suction tube and wherein suctioning is performed by covering the suction vent with a finger.

22. The method of claim 19, further comprising advancing the suction tube relative to the irrigation tube by moving the slide member in a distal direction.

23. The method of claim 22, wherein the suction tube is advanced to a point at or beyond a distal end of the irrigation tube.

24. The method of claim 23, wherein tactile feedback is provided to a user prior to advancement of the suction tube to a point at or beyond a distal end of the irrigation tube.

25. The method of claim 19, further comprising retracting the suction tube relative to the irrigation tube by moving the slide member in a proximal direction.

\* \* \* \* \*